United States Patent
Makino et al.

[11] Patent Number: 5,985,118
[45] Date of Patent: Nov. 16, 1999

[54] SOLID ELECTROLYTE GAS CONCENTRATION DETECTOR

[75] Inventors: Daisuke Makino, Ichinomiya; Keigo Mizutani; Hisayoshi Ohta, both of Okazaki; Yoshimasa Hijikata, Nishio; Kanehito Nakamura, Anjo; Hiroshi Mori, Ichinomiya, all of Japan

[73] Assignees: Nippon Soken, Inc.; Denso Corporation, both of Japan

[21] Appl. No.: 08/958,388

[22] Filed: Oct. 27, 1997

[30] Foreign Application Priority Data

Oct. 31, 1996 [JP] Japan .................................. 8-307385
Aug. 11, 1997 [JP] Japan .................................. 9-230375

[51] Int. Cl.$^6$ .................................................. G01N 27/26
[52] U.S. Cl. ...................... 204/426; 204/427; 204/428; 205/784.5; 205/787
[58] Field of Search .................................. 204/426, 425, 204/424, 427, 428; 205/781, 783.5, 784, 784.5, 787; 73/23.32

[56] References Cited

U.S. PATENT DOCUMENTS

| | | |
|---|---|---|
| 4,770,760 | 9/1988 | Noda et al. . |
| 4,875,981 | 10/1989 | Usami et al. .................. 204/425 |
| 4,927,517 | 5/1990 | Mizutani et al. ............... 204/425 |
| 5,217,588 | 6/1993 | Wang et al. .................. 204/426 |
| 5,304,294 | 4/1994 | Wang et al. .................. 204/426 |
| 5,397,442 | 3/1995 | Wachsman . |
| 5,493,896 | 2/1996 | Riegel . |
| 5,630,920 | 5/1997 | Friese et al. .................. 204/427 |
| 5,672,811 | 9/1997 | Kato et al. .................. 73/31.05 |
| 5,763,763 | 6/1998 | Kato et al. .................. 73/23.2 |

FOREIGN PATENT DOCUMENTS

| | | |
|---|---|---|
| 0678740 A1 | 10/1995 | European Pat. Off. . |
| 0731351 A2 | 9/1996 | European Pat. Off. . |
| 64-39545 | 2/1989 | Japan . |
| 4-359143 | 12/1992 | Japan . |
| 4-359144 | 12/1992 | Japan . |
| 4-359145 | 12/1992 | Japan . |
| 5-322844 | 12/1993 | Japan . |
| 2888873 | 11/1995 | United Kingdom . |

OTHER PUBLICATIONS

Technical Paper Series 960334 p. 3 (1996) Kato et al. Society of Automotive Engineers Inc. (month unknown).

Primary Examiner—Robert J. Warden, Sr.
Assistant Examiner—Kaj K. Olsen
Attorney, Agent, or Firm—Nixon & Vanderhye P.C.

[57] ABSTRACT

A gas concentration detector using solid electrolyte layers laminated measures a concentration of gas constituents in measuring gas such as exhaust gas of an internal combustion engine without being influenced by oxygen concentration in the measuring gas. The measuring gas is introduced into an inner cavity of the detector and outside air as a reference gas is introduced into an air passage in the detector. Oxygen concentration in the measuring gas in the inner cavity is maintained at a predetermined level by operation of an oxygen pumping cell constituted by an ion conductive solid electrolyte layer and a pair of electrodes formed on both surfaces of the layer. The oxygen concentration in the inner cavity is measured by an oxygen sensor cell having one electrode exposed to the inner cavity and the other electrode exposed to the reference gas. The concentration of the gas constituents in the measuring gas is measured in terms of ion current generated in a detector cell constituted by an ion conductive solid electrolyte layer and a pair of electrodes formed on both surfaces of the layer, one electrode being exposed to the measuring gas in the inner cavity and the other exposed to the reference gas in the air passage. Either one of the sensor cell and detector cell electrodes exposed to the measuring gas in the inner cavity is made of a material active to the gas constituents to be measured and the other electrode is made of a material inactive thereto.

16 Claims, 7 Drawing Sheets

SOLID ELECTROLYTE GAS CONCENTRATION DETECTOR

CROSS-REFERENCE TO RELATED APPLICATIONS

This application is based upon and claims benefit of priority of Japanese Patent Applications No. Hei-8-307385 filed on Oct. 31, 1996, and No. Hei-9-230375 filed on Aug. 11, 1997, the contents of which are incorporated herein by reference.

BACKGROUND OF THE INVENTION

1. Field of the Invention

The present invention relates to a solid electrolyte gas concentration detector which is mounted on an exhaust pipe of an internal combustion engine to detect concentration of gas constituents included in the exhaust gas.

2. Description of Related Art

Various technologies for controlling exhaust gas emission from an internal combustion engine have been known and used hitherto. For example, an air-fuel mixture supplied to an engine is controlled to be stoichiometric, and an exhaust gas from the engine is sent to a catalytic converter having three-way catalyst in which emissions such as hydro-carbon (HC), carbon-monoxide (CO) and nitrogen-oxides (NOx) are converted into harmless components. Recently, exhaust emission regulations have become stricter (as in OBD-II regulations), and a self-diagnostic system which gives warning to a driver when emission control devices including the three-way catalytic converter malfunction has to be installed on an vehicle. The driver is also required to repair the malfunctioning devices.

As a technology for detecting deterioration of the three-way catalytic converter, a two-$O_2$-sensor system is known in which one $O_2$ sensor is disposed upstream of the converter and the other $O_2$ sensor is disposed downstream thereof. However, as the emission regulations become much stricter from LEV (low emission vehicle) to ULEV (ultra low emission vehicle), the two-$O_2$-sensor system which detects indirectly a cleanup rate of the converter from signals of two $O_2$ sensors cannot detect it with a sufficiently high accuracy. Therefore, it is necessary to provide a gas concentration detector which directly detects components (HC, CO and NOx) in the emission with a high accuracy. It is also necessary to provide a gas concentration detector which can specifically detect methane ($CH_4$), because an engine which burns fuel including methane as a principal component (CNG engine) is being developed recently. Moreover, a gas concentration detector which is able to detect CO gas is required not only for the exhaust emission control system for an internal combustion engine but also for a fuel cell to detect CO coming out therefrom when methanol is decomposed.

Some kinds of gas detectors that directly detect gas concentration have been proposed. Such detectors utilize a oxygen ion conductive solid electrolyte, on both surfaces of which an electrode exposed to a reference gas and an electrode exposed to measuring gas are disposed, respectively, and voltage appearing between the electrodes is used for detecting gas concentration. This kind of gas detector detects the gas concentration from an amount of oxygen generated or consumed in the process of oxidization or reduction of the gas constituents. Since the oxidization or reduction in this kind of the detector is not selective to a specific gas constituent, oxygen concentration in the measuring gas has to be kept constant.

One of the gas detectors of this kind utilizing a solid electrolyte is disclosed in an SAE (Society of Automotive Engineers) paper, No. 960334. This is a thick film $ZrO_2$ sensor for detecting NOx gas. A oxygen detecting cell and a first pumping cell for exhausting oxygen are disposed in a first chamber into which measuring gas is introduced. A second pumping cell is disposed in a second chamber communicating with the first chamber through a diffusion resistance and driven by a predetermined voltage to exhaust oxygen in the chamber to an outside space. An electrode of the second pumping cell in the chamber is active for reducing NOx. Oxygen concentration change in the first chamber is detected by the oxygen detecting cell disposed therein and fed back to the driving voltage of the first pumping cell. In the second chamber, oxygen is newly generated by decomposition of NOx, and pumping current of the second pumping cell increases or decreases according to the concentration of NOx. The concentration of NOx is detected by measuring the pumping current. When this gas detector is used for detecting HC or CO, it is influenced by oxygen concentration in the chamber and calibration to eliminate oxygen influence is necessary because oxygen is consumed to oxidize HC or CO. In other words, this gas detector cannot avoid the influence of oxygen concentration in the measuring gas.

SUMMARY OF THE INVENTION

The present invention has been made in view of the above-mentioned problems, and an object of the present invention is to provide a solid electrolyte gas detector which is able to detect gas concentration without being influenced by oxygen concentration in the measuring gas.

The gas concentration detector according to the present invention consists of a sensor portion having a plug-like shape which is installed through an exhaust pipe wall and an electric circuit portion for controlling the sensor portion and detecting electric outputs from the sensor portion. The sensor portion includes a detector element made by laminating solid electrolyte layers and insulating spacer layers. The detector element is composed of an inner cavity into which the measuring gas is introduced through a hole having a certain diffusion resistance, an air passage into which outside air as a reference gas is introduced, an oxygen sensor cell to measure an oxygen concentration in the inner cavity, an oxygen pumping cell for controlling an oxygen concentration in the inner cavity at a predetermined level by feeding back the output from the oxygen sensor cell, and a detector cell through which an ion current proportional to gas constituents to be measured in the measuring gas flows. Each of the three cells is constituted by a solid electrolyte layer and a pair of electrodes formed on both sides of the solid electrolyte layer. The electric circuit portion includes a pumping cell controller circuit and an ion current detector circuit.

In case the gas concentration detector is designed to measure hydrocarbon (HC) concentration in the measuring gas, an oxygen sensor cell electrode exposed to the measuring gas in the inner cavity is made of a material which is active in oxidizing HC, such as platinum, and an detector electrode exposed to the measuring gas in the inner cavity is made of a material which is inactive in oxidizing HC, such as gold. HC contacting the surface of the sensor cell electrode is oxidized thereon consuming an amount of oxygen proportional to HC concentration in the measuring gas, while HC contacting the surface of the detector cell electrode is not oxidized thereon, thereby creating an oxygen concentration imbalance between the surfaces of both electrodes. As a voltage which is equal to the oxygen sensor voltage is applied to the detector cell, the excessive oxygen on the surface of the detector electrode is ionized and flows out through the solid electrolyte to the other detector electrode exposed to the reference gas in the air passage due to an oxygen partial pressure difference between the measuring gas and the reference gas, thereby generating ion current. Since the oxygen concentration in the measuring gas in the inner cavity is maintained at a constant level, the ion current is proportional to and represents HC concentration in the measuring gas and is not influenced by the oxygen concentration in the measuring gas. The materials of the sensor cell electrode and the detector cell electrode exposed to the measuring gas in the inner cavity may be reversed so that the detector cell electrode is active in oxidizing HC and the sensor cell electrode is inactive. In this case, oxygen shortage appears on the surface of the detector cell electrode and oxygen is supplied from the air passage to the inner cavity. The ion current proportional to the HC concentration in the measuring gas is generated in the same manner as described above.

The gas concentration detector according to the present invention may be designed to be suitable to measure a particular HC such as methane ($CH_4$). In this case, either the sensor cell electrode or the detector cell electrode exposed to the measuring gas in the inner cavity is made of a material (such as platinum) which is active to all HCs, and the other electrode is made of a material (such as a platinum alloy containing gold of 1 to 10 weight percent) which is inactive only to $CH_4$ and active to other HCs.

In order to minimize a measurement error of the HC concentration detector caused by carbon-monoxide (CO) contained in the measuring gas, an oxygen concentration level in the inner cavity is kept at a high side by setting the predetermined voltage level of the sensor cell in a range of 100 to 150 mV, because the error caused by CO becomes less when the oxygen concentration in the inner cavity is at a high side. On the other hand, the present invention may be applied to the gas concentration detector which is suitable to measure CO concentration. In this case, either the sensor cell electrode or the detector cell electrode exposed to the measuring gas in the inner cavity is made of a material which is active to CO, and the other electrode is made of a material which is inactive to CO, and preferably the oxygen concentration in the inner cavity is set at a low side by setting the predetermined voltage of the sensor cell at a high side, for example, 450 mV.

One of the pumping cell electrode exposed to the measuring gas in the inner cavity is preferably made of a material which is inactive to gas constituents to be measured to avoid any reaction of the gas constituents on the surface of the pumping cell electrode. The solid electrolyte layer constituting the sensor cell and the detector cell may be separated into two respective layers by an insulating spacer layer interposed therebetween or an insulating material to eliminate electric interference between the two cells.

Other objects and features of the present invention will become more readily apparent from a better understanding of the preferred embodiments described below with reference to the following drawings.

DETAILED DESCRIPTION OF THE PREFERRED EMBODIMENTS

Figure 1A:
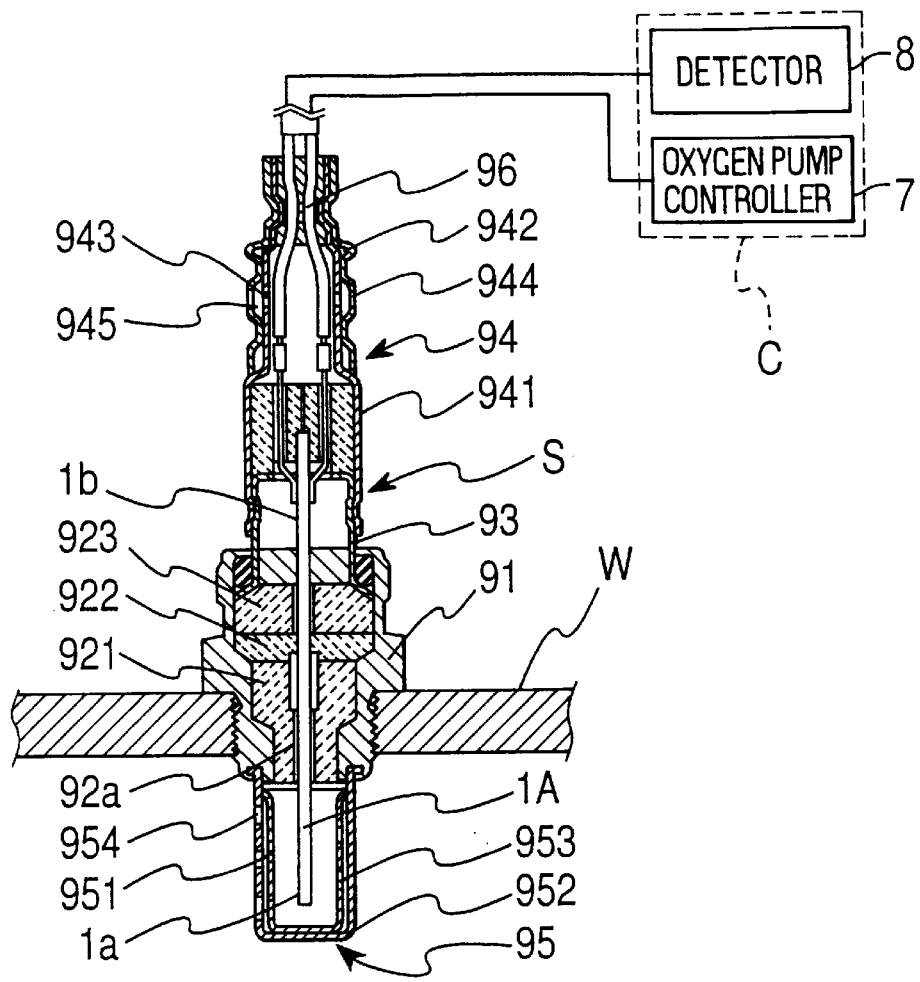
FIG. 1A is a cross-sectional view showing a whole structure of a solid electrolyte gas concentration detector as a first embodiment according to the present invention.

A first embodiment according to the present invention will be described, referring to FIGS. 1A–3. The first embodiment is designed to be suitable to detect HC concentration in the exhaust gas of an internal combustion engine. The gas concentration detector is composed of a sensor portion S which is installed at a position where the gas concentration is measured and an electric circuit portion C. The sensor portion S is installed through an exhaust pipe wall W with a housing 91 screwed therein. Insulators 921, 922 and 923 are disposed in the housing 91 and fixed therein by a cap 93. An elongated plate-shaped detector element 1A is disposed in a through-hole 92a formed in the insulators 921, 922 and 923. A tip portion 1a of the detector element 1A sticks out to a space inside the exhaust pipe wall W, and a base portion 1b of the detector element 1A sticks out upwardly from the cap 93.

The tip portion 1a of the detector element 1A is covered by an exhaust gas cover 95 having a cylindrical shape with a bottom end closed. The exhaust gas cover 95 is made of stainless steel and composed of an inner cover 951 and an outer cover 952, both covers having gas communicating holes 953 and 954 formed through cylindrical walls, respectively. An air cover 94 is fixed on the top of the cap 93. The air cover 94 is composed of a main cover 941 fixed to the cap 93 and a sub-cover 942 disposed on the top thereof. Both of the main cover 941 and the sub-cover 942 have air inlet holes 943 and 944 formed through respective peripheral walls thereof. Air serving as a reference gas is introduced into the air cover 94 through the air inlet holes 943 and 944. Air introduced in the cap 94 is led to the base portion 1b of the detector element 1A and further to the tip portion 1a. A water repellent filter 945 is disposed between the main cover 941 and sub-cover 942 at a position where the air inlet holes 943 and 944 are formed to prevent water from coming inside, and thereby only air is introduced into the sensor portion S. Lead wires 96 connected to the base portion 1b of the detector element 1A extends outside from the top portion of the air cover 94.

Figure 1B:
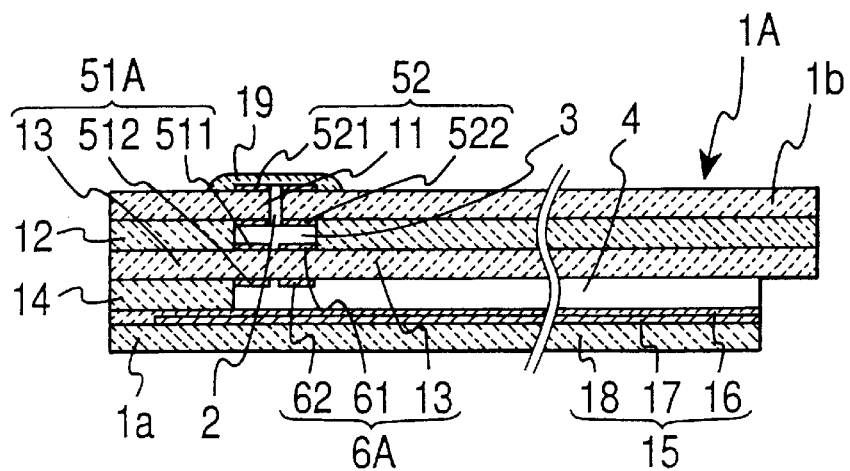
FIG. 1B is a cross-sectional view showing a detector element used in the detector shown in FIG. 1A.
Figure 2:
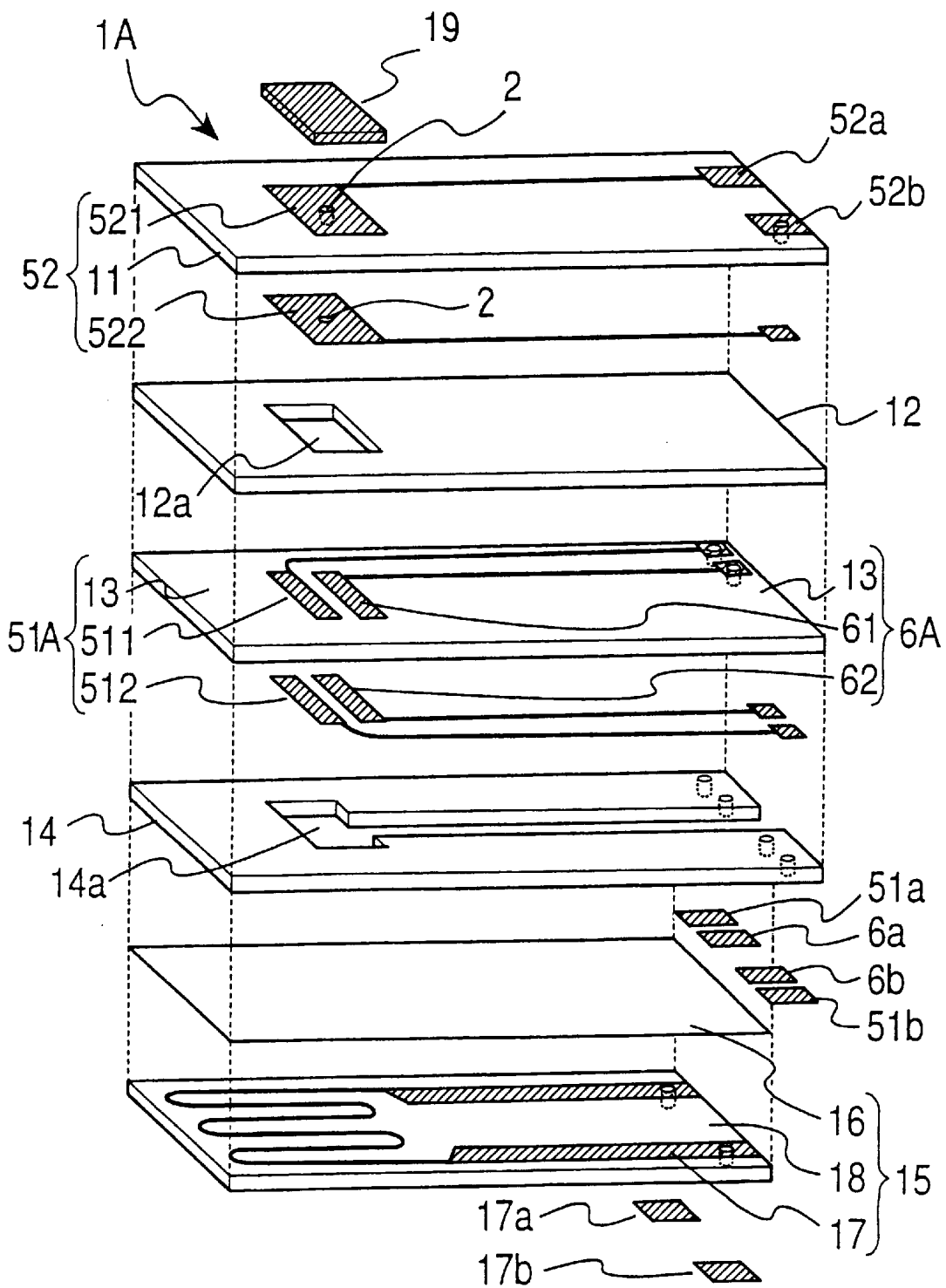
FIG. 2 is a perspective view showing component layers used in the detector element shown in FIG. 1B.

Referring to FIG. 1B and FIG. 2, details of the detector element 1A will be described. FIG. 1B shows an enlarged cross-section of the detector element 1A, and FIG. 2 shows component layers of the detector element 1A, separated from each other. The detector element 1A has an inner cavity 3 formed at a position close to the tip of the detector element (left side of FIG. 1B), an oxygen sensor cell 51A, an oxygen pumping cell 52 and a detector cell 6A. Component layers constituting these cells are superimposed on each other. An oxygen ion conductive solid electrolyte layer 11, a flat insulating spacer layer 12 made of alumina and another oxygen ion conductive solid electrolyte layer 13 are superimposed on each other in this order from the top. A window 12a is formed on the spacer layer 12 for forming the inner cavity 3 together with both solid electrolyte layers 11 and 13 when superimposed.

Underneath the solid electrolyte layer 13, an insulating spacer layer 14 made of alumina and a flat heater layer 15 are disposed in this order. A window 14a is formed on the spacer layer 14 at a position corresponding to the window 12a on the spacer layer 12, and a slit is also formed thereon and connected to the window 14a. When the spacer layer 14 is sandwiched between the solid electrolyte layer 13 and the heater layer 15, the window 14a and the slit form an air passage through which air as a reference gas is introduced into the detector element 1A.

A pair of pumping cell electrodes 521 and 522 are formed on and underneath the solid electrolyte layer 11, respectively, by a printing process such as a screen printing at the position corresponding to the window 12a of the spacer layer 12. The electrode 521 is made of platinum (Pt), and the electrode 522 is made of gold (Au). The solid electrolyte layer 11, and the pair of pumping cell electrodes 521 and 522 constitute the pumping cell 52. At the center of the pair of pumping cell electrodes 521 and 522, a pin holes 2 are formed. A pin hole is also formed on the solid electrolyte layer 11 at a position corresponding to the pin holes 2 of the electrodes. The measuring gas is introduced into the inner cavity 3 through the pin holes 2. When oxygen is selectively pumped out from the inner cavity 3 by operation of the pumping cell 52, oxygen concentration in the inner cavity 3 becomes different from that in the outside of the cavity 3 because of a diffusion resistance of the pin holes 2. A pair of sensor cell electrodes 511 and 512 are formed on and underneath the solid electrolyte layer 13 at a position corresponding to the left half of the window 12a. Both of the sensor cell electrodes 511 and 512 are made of platinum having an approximately half size of the first electrodes 521 and 522. Similarly, a pair of detector cell electrodes 61 and 62 are formed on and underneath the solid electrolyte layer 13 at a position corresponding to the right half of the window 12a. The detector cell electrode 61 is made of gold and the other electrode 62 is made of platinum, both having an approximately half size of the pumping cell electrodes. The pair of the sensor cell electrodes 511 and 512, and the solid electrolyte layer 13 constitute the sensor cell 51A. The pair of the third electrodes 61 and 62, and the solid electrolyte layer 13 constitute the detector cell 6A.

A heater layer 15 is disposed underneath the spacer layer 14 for heating the detector element to increase a sensitivity of the detector. The heater layer 15 is composed of an alumina substrate 18 with platinum heating layer 17 printed thereon and an alumina cover layer 16. On the base portion 1b of the detector element 1A, terminals 52a and 52b for the pumping cell electrodes 521 and 522, terminals 51a and 51b for the sensor cell electrodes 511 and 512, terminals 6a and 6b for the detector cell electrodes 61 and 62, and terminals 17a and 17b for the heating layer 17 are formed respectively. A protective layer 19 made of a porous material such baked porous alumina is disposed on the solid electrolyte layer 11 to prevent large size particulates such as carbon soot from entering into the pin hole 2.

The solid electrolyte layers 11 and 13 are made of yttria added zirconia and formed into a flat sheet in a sheet forming process such as a DOCTOR BLADE method. These layers are usually formed with a thickness of 50~300 $\mu$m, however, it is preferable to form them with a thickness of 100~200 $\mu$m, considering the balance of the electric resistance and the mechanical strength of the sheet. The thickness of the electrodes is usually selected in a range from 1 to 20 $\mu$m, preferably in a range from 5 to 10 $\mu$m from a standpoint of heat-resistance and gas diffusion.

Figure 3:
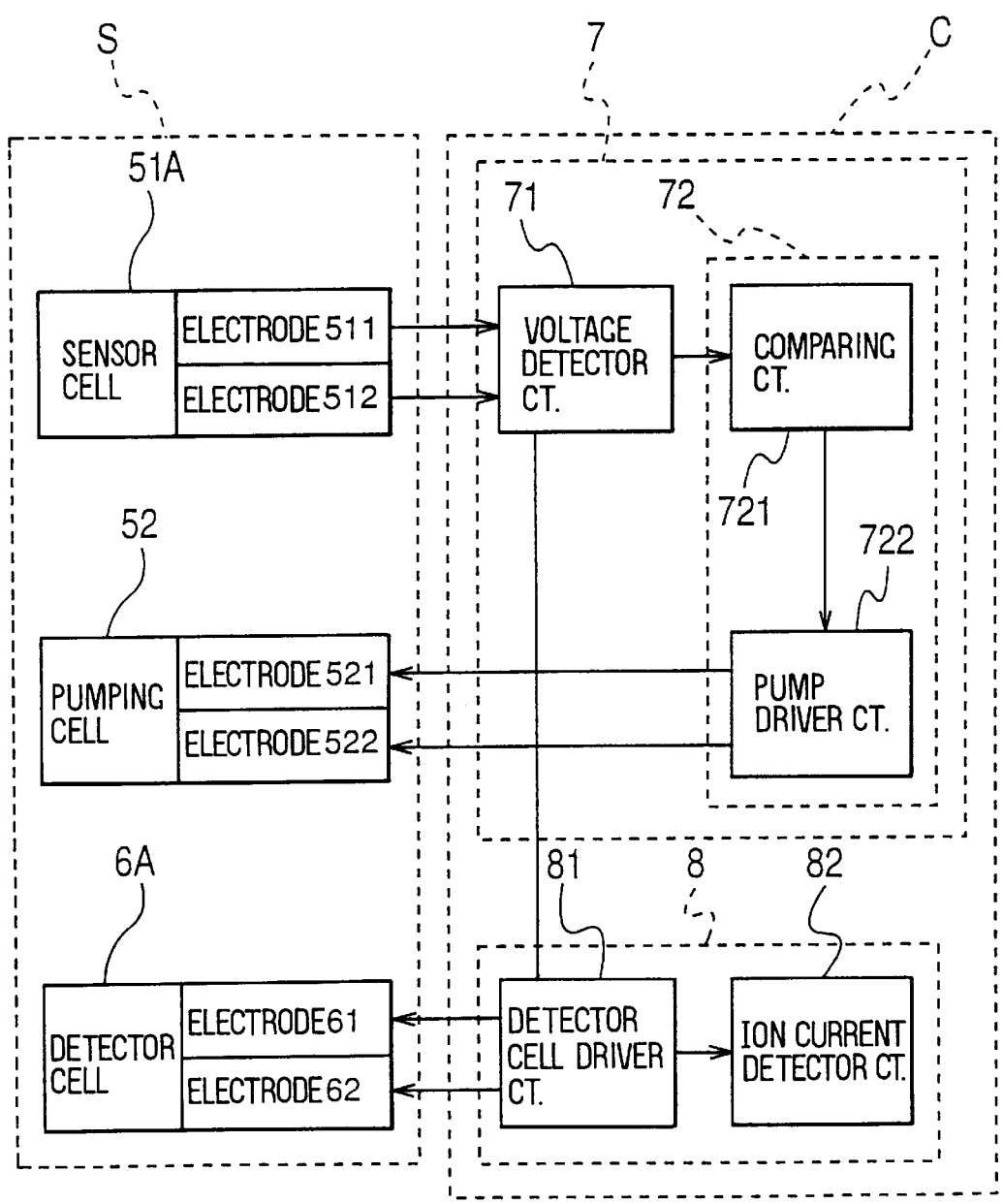
FIG. 3 is a block diagram showing the detector and electric circuits therefor.

FIG. 3 is a block diagram of the gas detector including the sensor portion S and the electric circuit portion C. The electric circuit portion C consists of an oxygen pumping cell controller 7 and a signal detecting portion 8. The oxygen pumping cell controller 7 includes a voltage detector circuit 71 which detects the voltage generated in the sensor cell 51A and appearing between the pair of the sensor cell electrodes 511 and 512, and a pumping cell control circuit 72 which controls the pumping cell 52 according to the output from the voltage detector circuit 71. The pumping cell control circuit 72 includes a comparing circuit 721 and a pump driver circuit 722. The comparing circuit 721 compares the voltage fed from the voltage detector circuit 71 with a predetermined standard voltage and outputs the difference voltage therebetween to a pump driver circuit 722. The pump driver circuit 722 supplies a driving voltage which represents the difference voltage to the pair of the pumping cell electrodes 521 and 522 of the pumping cell 52. The signal detecting portion 8 includes a detector cell driver circuit 81 which supplies a driving voltage to the pair of the detector cell electrodes 61 and 62 of the detector cell 6A and an ion current detector circuit 82 which detects ion current flowing in the detector cell 6A. The voltage generated in the sensor cell 51A is fed to the detector cell driver circuit 81 from the voltage detector circuit 71, and this voltage is supplied to the detector cell 6A.

The operation of the first embodiment will be described, referring to FIGS. 1A~3. The exhaust gas in the exhaust pipe is introduced into the inner space of the exhaust gas cover 95 through the gas communicating holes 953 and 954 as the measuring gas. The measuring gas enters into the inner cavity 3 through the protecting layer 19 and the pin hole 2 of the detector element 1A. On the other hand, outside air is introduced into the air passage 4 through the air inlet holes 943 and 944 disposed on the air cover 44 as the reference gas. One of the sensor cell electrodes 512 of the sensor cell 51A and one of the detector cell electrodes 62 are exposed to the reference gas introduced into the air passage 4.

In case one of the pumping cell electrode 521 is positive and the other electrode 522 is negative, oxygen in the inner cavity 3 receives electrons from the electrode 522, moves through the solid electrolyte layer 11 and releases the electrons to the electrode 521, and then the oxygen is discharged into the exhaust gas through the protecting cover 19. As a result, the oxygen concentration in the inner cavity 3 decreases because oxygen diffusion from the exhaust gas to the inner cavity is restricted by the pin hole 2. In other words the oxygen in the inner cavity 3 is pumped out by the operation of the pumping cell 52.

Between the sensor cell electrodes 511 and 512 of the sensor cell 51A, a voltage proportional to a difference between the oxygen partial pressure in the inner cavity 3 and that in the air passage 4 is generated. This voltage is detected by the voltage detector circuit 71 and fed to the comparing circuit 72. The comparing circuit 72 compares the voltage fed with a predetermined standard voltage and outputs the difference voltage therebetween to the pump driver circuit 722. The pump driver circuit 722 supplies the difference voltage to the pumping cell 52, so that the pumping cell 52 pumps out oxygen from the inner cavity 3 or sucks in oxygen into the inner cavity 3 to maintain the oxygen concentration in the inner cavity 3 at a constant level.

One of the sensor cell electrodes 511 and one of the detector cell electrodes 61 are equally exposed to the measuring gas in the inner cavity 3, because both electrodes are positioned symmetrically with respect to the pin hole 2. In other words, both electrodes 511 and 61 are exposed to the same level of oxygen concentration. The oxygen in the inner cavity 3 contacting the electrode 511 is consumed locally on the electrode 511 by oxidizing HC gas since the electrode 511 is made of platinum which is active to HC gas, while the oxygen contacting the electrode 61 is not consumed thereon since the electrode 61 is made of gold which is not active to HC gas. Therefore, the voltage appearing between the sensor cell electrodes 511 and 512 of the sensor cell 51A becomes different from the voltage appearing between the detector cell electrodes 61 and 62 of the detector cell 6A. In other words, the voltage between the detector cell electrodes 61 and 62 of the detector cell 6A (detector voltage) becomes smaller than the voltage between the sensor cell electrodes 511 and 512 of the sensor cell 51A (sensor voltage) by an amount proportional to the amount of the oxygen consumed on the electrode 511. On the other hand, the detector cell driver circuit 81 supplies a voltage to the detector cell 6A to equalize the detector voltage to the sensor voltage. Accordingly, excessive oxygen in contact with the detector cell electrode 61 in the inner cavity 3 is purged out into the air passage 4 through the solid electrolyte layer 13. The excessive oxygen purged out through the solid electrolyte 13 generates ion current between the detector cell electrodes 61 and 62 which is proportional to the HC concentration in the inner cavity 3. The ion current is detected by the ion current detector circuit 82.

Figure 4:
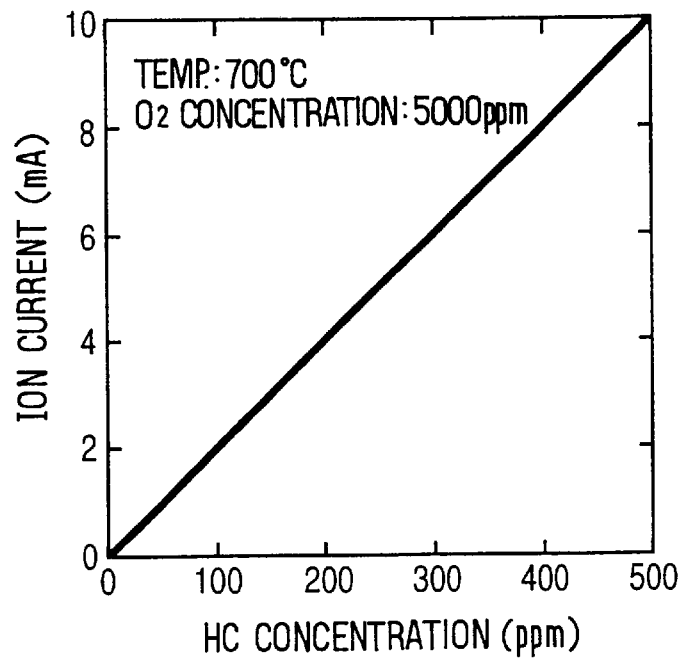
FIG. 4 is a graph showing relation between HC concentration and ion current in the detector shown in FIG. 1A.

In case the HC concentration in the inner cavity 3 is zero, there is no difference between the sensor voltage and the detector voltage, and accordingly no ion current is detected. Therefore, there is no offset of the ion current. Moreover, the HC gas in the inner cavity 3 is not oxidized on the surface of the pumping cell electrode 522 because the electrode 522 is made of gold which is inactive to HC, and accordingly the HC concentration in the inner cavity 3 does not change. FIG. 4 is a graph showing relation between the HC concentration in the measuring gas and ion current actually detected by the ion current detector circuit 82. As seen in the graph, ion current is exactly proportional to the HC concentration, and there is no offset current.

Though the sensor cell electrode 511 is made of platinum and the detector cell electrode 61 is made of gold in the embodiment described above, the materials of both electrodes may be reversed. That is, the sensor cell electrode 511 may be made of gold which is inactive to HC and the detector cell electrode 61 may be made of platinum which is active to HC. In this case, oxygen in the inner cavity 3 is consumed on the surface of the detector cell electrode 61 by oxidizing HC, while no oxygen is consumed on the surface of the sensor cell electrode 511. Therefore, the detector voltage becomes higher than the sensor voltage. Since the detector cell driver circuit 81 supplies a voltage to the detector cell 6A to equalize the sensor and detector voltages, shortage of oxygen on the surface of the detector cell electrode 61 is compensated by sending oxygen from the air passage 4 to the inner cavity 3 through the solid electrolyte layer 13, thereby generating ion current through the solid electrolyte layer 13. The ion current proportional to the HC concentration is detected by the ion current detector circuit 82 in the same manner as described above.

Figure 5:
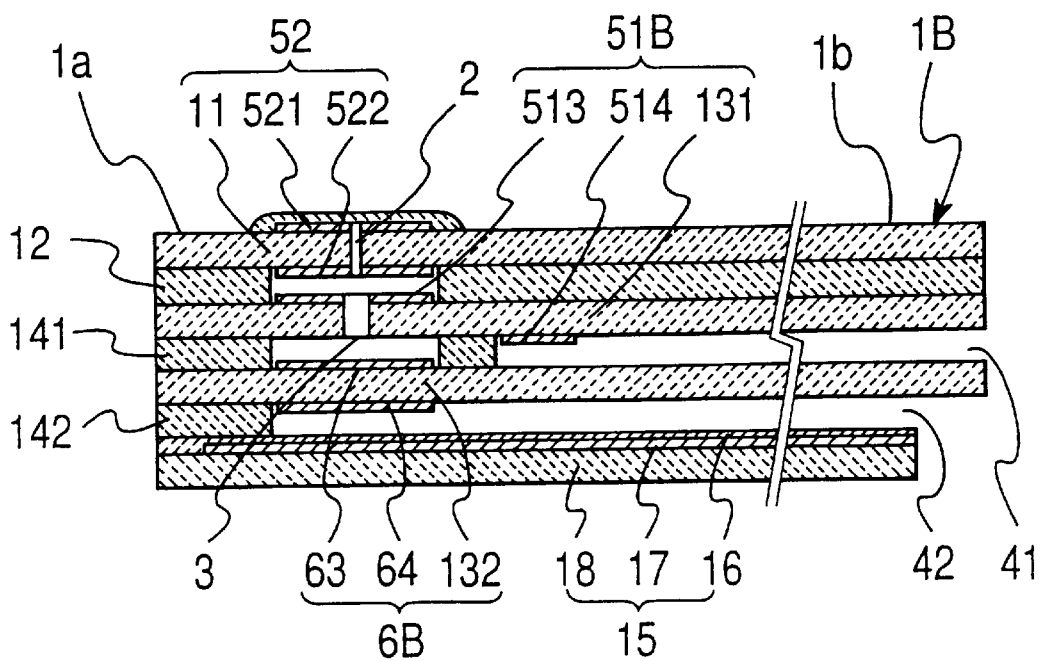
FIG. 5 is a cross-sectional view showing a detector element of a second embodiment according to the present invention.
Figure 6:
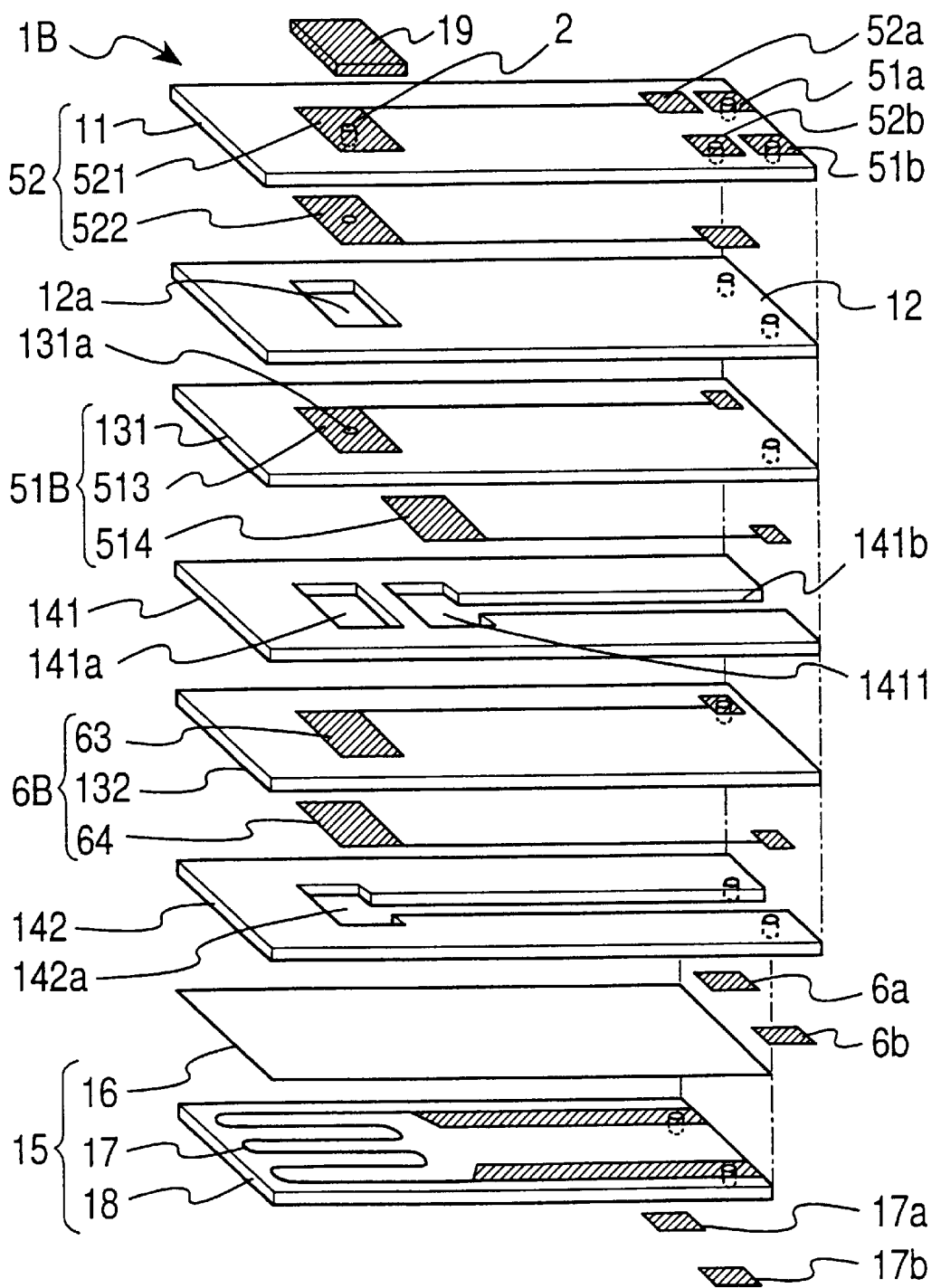
FIG. 6 is a perspective view showing component layers used in the detector element of the second embodiment.

Referring to FIGS. 5 and 6, a second embodiment according to the present invention will be described. In this embodiment, the sensor cell 51A and the detector cell 6A of the first embodiment are replaced with a sensor cell 51B and a detector cell 6B, respectively, and other structures are the same or similar to those of the first embodiment. The parts and components which are the same as those in the first embodiment are numbered with the same number in the drawings. The following explanation will be made only for different structures and functions.

The detector element 1B of the second embodiment is made by superimposing various layers on each other as in the first embodiment. Three solid electrolyte layers 11, 131 and 132, and three insulating spacer layers 12, 141 and 142 are superimposed as shown in FIGS. 5 and 6. A square window 12a and another square window 141a are formed on the spacer layers 12 and 141, respectively, at a position right under the pin hole 2. A round hole 131a is formed on the solid electrolyte layer 131, which is sandwiched between the spacer layers 12 and 141, at a position corresponding to the pin hole 2. The windows 12a and 141a form a inner cavity 3 together with solid electrolyte layers 11 and 132. The inner cavity 3 is composed of an upper cavity and a lower cavity, both being communicated with each other through the round hole 131a. An opening 1411 is formed on the spacer layer 141 and connected to a slit 141b. The opening 1411 and the slit 141b constitute a first air passage 41 together with the solid electrolyte layers 131 and 132. The first air passage 41 introduces air from the outside as the reference gas. Another opening 142a including a longitudinally extended slit is formed on the spacer layer 142 at a position corresponding to the window 141a. The opening 142a is sandwiched between the solid electrolyte layer 132 and a heater layer 15, thereby constituting a second air passage 42 into which air is introduced from the outside as a reference gas.

The sensor cell 51B is constituted by the solid electrolyte layer 131 and a pair of sensor cell electrodes 513 and 514 formed on both sides of the solid electrolyte layer 131. The sensor cell electrode 513 is formed at a position corresponding to the pumping cell electrode 522 and has the same shape as that of the pumping cell electrode 522. The other sensor cell electrode 514 is formed at a position corresponding to the opening 1411. The detector cell 6B is constituted by the solid electrolyte layer 132 and a pair of detector cell electrodes 63 and 64 formed on both surfaces of the solid electrolyte layer 132. Both of the detector electrodes 63 and 64 have the same shape as that of the pumping cell electrodes 521 and 522. Both detector cell electrodes 63 and 64 are formed at a position corresponding to the window 141a and the opening 142a. The electric circuit portion of the second embodiment is substantially the same as that of the first embodiment.

In the second embodiment, outside air as a reference gas is introduced into both air passages 41 and 42. The sensor cell 51B generates a voltage which is proportional to oxygen concentration difference between the inner cavity 3 into which the measuring gas is introduced and the first air passage 41 into which outside air as a reference gas is introduced. Therefore, the voltage generated in the sensor cell 51B (sensor voltage) represents oxygen concentration of the measuring gas. The voltage between the detector cell electrodes 63 and 64 (detector voltage) is controlled so that it becomes the same level as the sensor voltage in the same manner as in the first embodiment. Therefore, ion current proportional to the HC concentration in the measuring gas flows in the sensor cell 6B. Since the sensor cell 51B and the detector cell 6B are electrically insulated from each other by the spacer layer 141, detection accuracy is further improved.

The foregoing embodiments may be modified in forms as exemplified in the following. The first embodiment in which the sensor cell 51A and the detector cell 6A is formed on the same solid electrolyte layer 13 may be modified so that a portion of the solid electrolyte layer carrying the sensor electrodes and the other portion carrying the detector electrodes are insulated from each other by inserting an insulator therebetween. In the detector element thus modified, electric interference between the sensor cell and the detector cell will be prevented. Though the foregoing embodiments are designed to be suitable to detect HC, they can be used also for detecting CO in the exhaust gas from an internal combustion engine. Either one of the sensor electrode or detector electrode facing the inner cavity is made of a material which is active to oxidize the gas constituents in the foregoing embodiments. However, this electrode material may be replaced with a material to which oxidization activity is added by forming a catalytic layer including a noble metal on the surface of a metallic layer. Though all the cells including the sensor cell, the detector cell and other cells are integrated in a single body in the foregoing embodiments, these cells may be separated into several bodies. Though the oxygen pumped out by the pumping cell is exhausted to the measuring gas in the foregoing embodiments, it may be purged out into the outside air. In this case, an oxygen purging hole has to be made separate from the air passage so that the purged oxygen does not affect the oxygen concentration of the air used as a reference gas. The oxygen pumping cell controller is not limited to the form described above, but other controllers may be used as far as they control the pumping cell based on the sensor cell output representing the oxygen level in a feed back fashion. The control of the pumping cell is not limited to the control by a level of supplied voltage, but the pumping cell may be controlled by a duty ratio of the supplied voltage.

Figure 7:
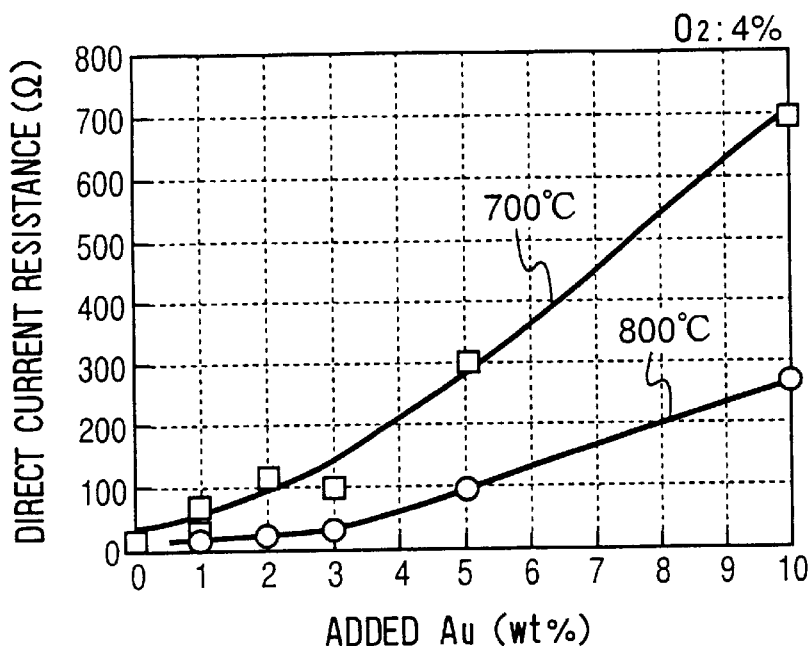
FIG. 7 is a graph showing relation between a percentage of added gold to a detecting cell electrode and direct current resistance of the detecting cell in a third embodiment according to the present invention.
Figure 8:
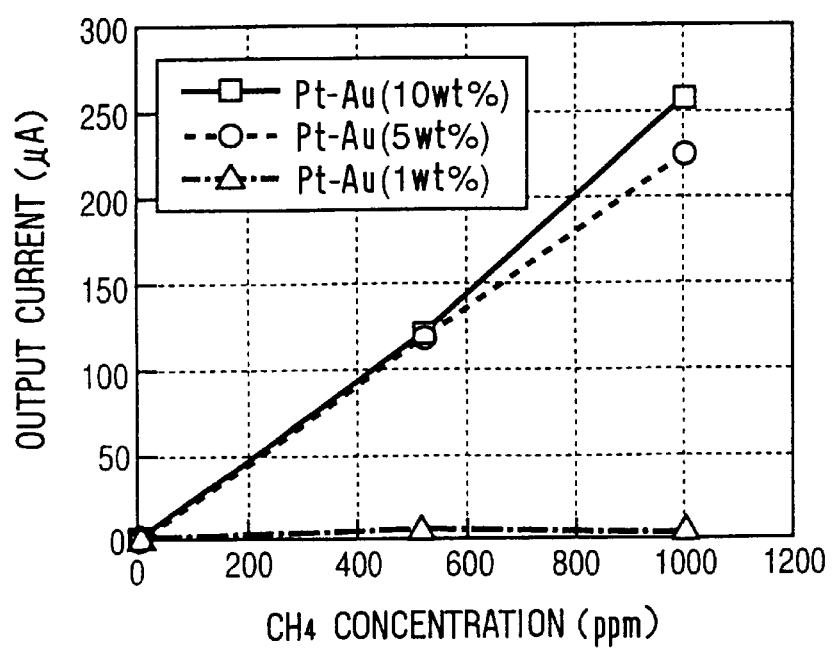
FIG. 8 is a graph showing relation between methane concentration and output current of the detector in the third embodiment.

Referring to FIGS. 7 and 8, a third embodiment of the present invention will be described. The structure of the third embodiment is the same as that of the first embodiment shown in FIGS. 1–3, except the material of the detector cell electrode 61 of the detector cell 6A. The third embodiment is designed to be suitable to detect methane ($CH_4$) concentration in an engine which burns fuel containing methane as a principal gas. The detector electrode 61 of the third embodiment is made of gold-added platinum (Au-added Pt) as opposed to the detector electrode of the first embodiment which is made of gold.

The gold electrode is inactive to all kinds of HC while the platinum electrode is active thereto. When gold is added to a platinum base electrode, its oxidization activity decreases. The larger the amount of gold added to the platinum electrode becomes, the less active the electrode becomes. Since methane is the least active among various hydrocarbons, the gold-added platinum electrode becomes inactive to methane with a low percentage of added gold, while the electrode is still active to other hydro-carbons. Therefore, an oxidization activity difference between the sensor cell electrode 511 (Pt electrode) and the detector cell electrode 61 (Au-added Pt) appears with a low percentage of added gold with respect to methane.

FIG. 7 shows relation between the percentage of added gold and a direct current resistance of the detector cell 6A. The direct current resistance is a sum of an electric resistance of the solid electrolyte 13 and an electrode reaction resistance appearing when oxygen is ionized and enters into the solid electrolyte 13. As seen in the graph in FIG. 7, the direct current resistance increases as the percentage of the added gold increases. If the percentage of added gold is in excess of 10% in weight, the direct current resistance becomes too high to obtain sufficient detecting current to secure a required accuracy. FIG. 8 shows relation between methane concentration and output current (ion current detected by the detector circuit 82), in which the percentage of the added gold is selected at three levels, 1%, 5% and 10% in weight. As seen from the graph, when the added gold is 1% the output current to detect the methane concentration is not obtained because the activity difference between the sensor cell electrode 511 and the detector cell electrode 61 is not sufficient. When the percentage of the added gold is 5% and 10%, the output current enough to detect the methane concentration is obtained with a sufficient linearity. When the percentage is in a range higher than 1% and lower than 5%, the methane concentration can be selectively detected in a measuring gas containing other hydro-carbons such as propane, though detection sensitivity is not as high as in the cases of 5% and 10%.

Figure 9:
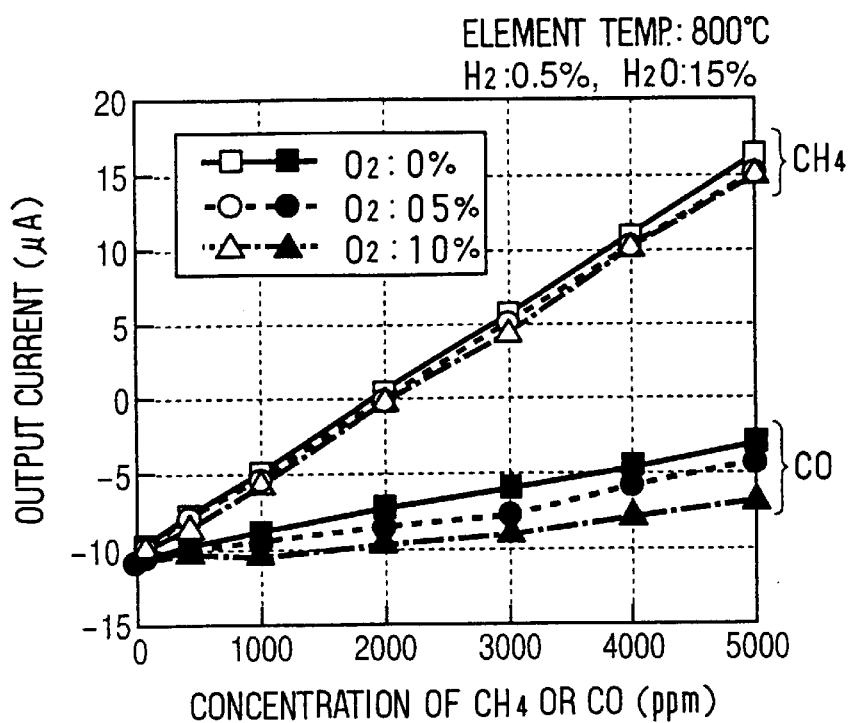
FIG. 9 is a graph showing relation between concentration of methane or carbon-monoxide and output current of the detector in the third embodiment.
Figure 10:
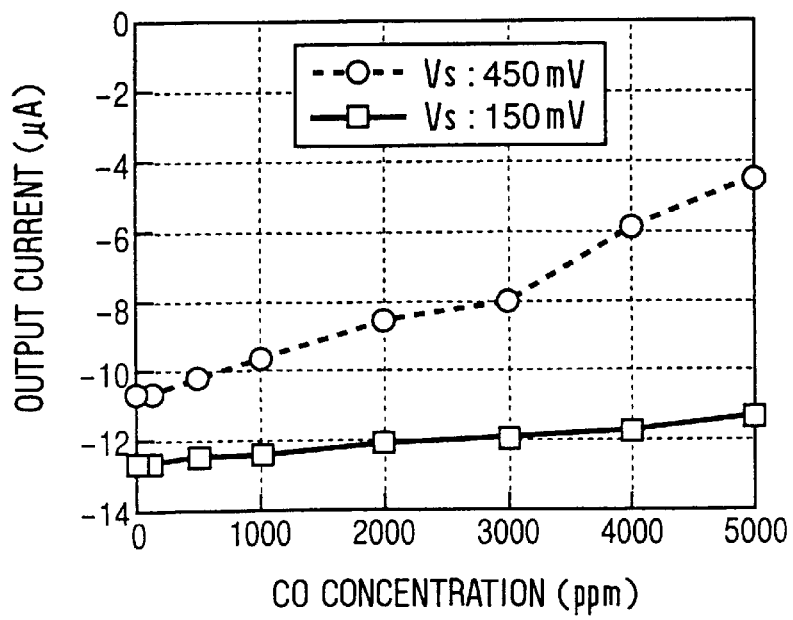
FIG. 10 is a graph showing relation between carbon-monoxide concentration and output current of the detector in a fourth and a fifth embodiment according to the present invention.

In the foregoing embodiments, the HC concentration in the measuring gas is detected by using different materials having different oxidation activity to HC, respectively for the sensor electrode and the detector electrode both facing the cavity 3 where the measuring gas is introduced. For example, in the third embodiment, the sensor electrode 511 is made of platinum and the detector electrode 61 is made of gold-added platinum. Because the oxidation activity of both electrodes is different from each other not only to HC but also to carbon-monoxide (CO), the ion current representing HC concentration detected by the detector circuit 82 includes some error resulting from CO concentration. A fourth embodiment according to the present invention is a gas concentration detector which is designed to minimize the error due to the CO concentration in the measuring gas. FIG. 9 shows relation between $CH_4$ or CO concentrations and the output current (detected ion current) in the third embodiment, where the predetermined standard voltage of the sensor cell 51A is 450 mV. As seen in the graphs, the output current increases as the CO concentration increases though the sensitivity to the CO concentration is not as sharp as that to $CH_4$ concentration. This means that the $CH_4$ concentration detector includes some error due to CO. In the course of experiments, it has been found out that the amount of error resulting from CO depends on oxygen concentration in the inner cavity 3 as seen in FIG. 9. To minimize the error, the predetermined standard voltage of sensor cell 51A is set in a range from 100 to 150 mV in the fourth embodiment. The reason the standard voltage is set higher than 100 mV is that it is difficult to maintain the oxygen concentration in the inner cavity 3 if the standard voltage is too low. FIG. 10 shows relation between the CO concentration and the output current, comparing two cases where the standard voltage is set at 150 mV and 450 mV. As seen in the graph, the sensitivity to CO concentration is very low or almost negligible when the standard voltage is set at 150 mV, while the output current increases as CO concentration becomes higher when the standard voltage is set at 450 mV. The same idea as in the fourth embodiment is also applicable to the first and second embodiments which are designed to detect hydro-carbons not limited to $CH_4$.

As opposed to the fourth embodiment, a fifth embodiment according to the present invention is designed to be suitable to detect CO concentration. The CO concentration detector will be used for detecting CO exhausted from a fuel cell, for example. In order to make the detector sensible to CO concentration as seen in FIG. 10, the predetermined standard voltage of the sensor cell of the fifth embodiment is set at a higher level than that of the HC detector, for example, at 450 mV.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A solid electrolyte gas concentration detector for measuring a constituent gas concentration in measuring gas, the detector comprising:

an inner cavity into which measuring gas is introduced through a passage;

a reference gas passage into which a reference gas is introduced;

a first oxygen ion conductive solid electrolyte layer having a pair of sensor cell electrodes formed on both surfaces thereof, one of said sensor cell electrodes being exposed to the measuring gas in the inner cavity and the other of said sensor cell electrodes being exposed to the reference gas in the reference gas passage, and a pair of detector cell electrodes formed on both surfaces thereof, one of said detector cell electrodes being exposed to the measuring gas in the inner cavity and the other of said detector cell electrodes being exposed to the reference gas in the reference gas passage, the first electrolyte layer and the pair of sensor cell electrodes constituting an oxygen sensor cell, the first electrolyte layer and the pair of detector cell electrodes constituting a detector cell, said one of the oxygen sensor cell electrodes exposed to the measuring gas in the inner cavity being made of a material which is reactive with said constituent gas, said one of the detector cell electrodes exposed to the measuring gas in the inner cavity being made of a material which is inactive with said constituent gas;

an insulating spacer layer which has the inner cavity formed therein laminated on the first solid electrolyte;

a second oxygen ion conductive solid electrolyte layer having a pair of pumping cell electrodes formed on both surfaces thereof, one of said pumping cell electrodes being exposed to the measuring gas in the inner cavity and the other of said pumping cell electrodes being exposed to the measuring gas, the second electrolyte layer and the pair of the pumping cell electrodes constituting a pumping cell, the second electrolyte layer being laminated on the first electrolyte layer with the insulating spacer layer interposed therebetween;

an oxygen pumping cell controller for controlling oxygen concentration in the inner cavity according to an output voltage of the oxygen sensor cell in a feed back fashion;

a detector cell driver for supplying the same level of voltage as the voltage sensed by the oxygen sensor cell to the detector cell, so that the detector cell pumps out oxygen which exists on and around a surface of said one of the detector cell electrodes exposed to the measuring gas, from the inner cavity to the reference gas passage; and an ion current detector for measuring ion current flowing through the first electrolyte, which represents the concentration of said constituent gas in the measuring gas, by detecting a current in the detector cell caused by the voltage supplied from the detector cell driver to the detector cell.

2. A solid electrolyte gas concentration detector according to claim 1, wherein said one of the oxygen sensor cell electrodes exposed to the measuring gas in the inner cavity is made of a material which is active in oxidizing hydrocarbons, and said one of the detector cell electrodes exposed to the measuring gas in the inner cavity is made of a material which is inactive in oxidizing hydro-carbons.

3. A solid electrolyte gas concentration detector according to claim 2, wherein said one of the oxygen sensor cell electrodes which is active in oxidizing hydrocarbons is made of platinum, and said one of the detector cell electrodes which is inactive in oxidizing hydro-carbons is made of gold.

4. A solid electrolyte gas concentration detector according to claim 2, wherein the oxygen pumping cell controller controls the oxygen concentration in the inner cavity so that an voltage generated by the oxygen sensor cell is maintained in a predetermined range from 100 mV to 150 mV.

5. A solid electrolyte gas concentration detector according to claim 1, wherein said one of the sensor cell electrodes is active in oxidizing hydro-carbons and is made of platinum, and said one of the detector cell electrodes is inactive in oxidizing methane and is made of platinum alloy containing gold in excess of 1 weight-percent and less than 10-weight percent.

6. A solid electrolyte gas concentration detector according to claim 1, wherein said one of the oxygen sensor cell electrodes exposed to the measuring gas in the inner cavity is made of a material which is active in oxidizing carbon-monoxide, and said one of the detector cell electrodes exposed to the measuring gas in the inner cavity is made of a material which is inactive in oxidizing carbon-monoxide.

7. A solid electrolyte gas concentration detector according to claim 1, wherein the one electrode of the oxygen pumping cell exposed to the measuring gas in the inner cavity is made of a material which is inactive to the gas constituent to be measured.

8. A solid electrolyte gas concentration detector according to claim 1, wherein the passage through which the measuring gas is introduced into the inner cavity has a diffusion resistance.

9. A solid electrolyte gas concentration detector according to claim 1, wherein the oxygen sensor cell generates a voltage according to oxygen gas concentration in the inner cavity and the reference gas passage.

10. A solid electrolyte gas concentration detector according to claim 1, wherein the oxygen pumping cell controller controls a driving voltage for the oxygen pumping cell, so that a voltage generated in the oxygen sensor cell maintains a constant level to keep oxygen concentration in the inner cavity substantially constant.

11. A solid electrolyte gas concentration detector for measuring a constituent gas concentration in measuring gas, the detector comprising:

an inner cavity into which measuring gas is introduced through a passage;

a first and second reference gas passage into which a reference gas is introduced;

a first oxygen ion conductive solid electrolyte layer portion having a pair of sensor cell electrodes formed on both surfaces thereof, one of said sensor cell electrodes being exposed to the measuring gas in the inner cavity and the other of said sensor cell electrodes being exposed to the reference gas in the first reference gas passage, said first portion and said pair of sensor cell electrodes constituting an oxygen sensor cell, and a second oxygen ion conductive solid electrolyte layer portion having a pair of detector cell electrodes formed on both surfaces thereof, one of said detector cell electrodes being exposed to the measuring gas in the inner cavity and the other of said detector cell electrodes being exposed to the reference gas in the second reference gas passage, said second portion and said pair of detector cell electrodes constituting a detector cell, said first and second electrolyte layer portions having an insulating material disposed therebetween, said one of the oxygen sensor cell electrodes exposed to the measuring gas in the inner cavity being made of a material which is reactive with said constituent gas, said one of the detector cell electrodes exposed to the measuring gas in the inner cavity being made of a material which is inactive with said constituent gas;

a first insulating spacer layer which has the inner cavity formed therein laminated on said first electrolyte layer portion;

a third oxygen ion conductive solid electrolyte layer portion having a pair of pumping cell electrodes formed on both surfaces thereof, one of said pumping cell electrodes being exposed to the measuring gas in the inner cavity and the other of said pumping cell electrodes being exposed to the measuring gas, the third electrolyte layer portion and the pair of the pumping cell electrodes constituting a pumping cell, the third electrolyte layer portion being laminated on the first electrolyte layer portion with the first insulating spacer layer interposed therebetween;

an oxygen pumping cell controller for controlling oxygen concentration in the inner cavity according to an output voltage of the oxygen sensor cell in a feed back fashion;

a detector cell driver for supplying the same level of voltage as the voltage sensed by the oxygen sensor cell to the detector cell, so that the detector cell pumps out oxygen which exists on and around a surface of said one of the detector cell electrodes exposed to the measuring gas, from the inner cavity to the reference gas passage; and an ion current detector for measuring ion current flowing through the second electrolyte portion, which represents the concentration of said constituent gas in the measuring gas, by detecting a current in the detector cell caused by the voltage supplied from the detector cell driver to the detector cell.

12. A solid electrolyte gas concentration detector according to claim 11, wherein the first and second ion conductive solid electrolyte layer portions are first and second laminated layers and said insulating material is a second insulating spacer layer that is interposed therebetween, said first layer constituting the oxygen sensor cell together with the pair of the oxygen sensor cell electrodes, the second layer constituting the detector cell together with the pair of the detector cell electrodes.

13. A solid electrolyte gas concentration detector for measuring a constituent gas concentration in measuring gas, the detector comprising:

an inner cavity into which measuring gas is introduced through a passage;

at least one reference gas passage into which a reference gas is introduced;

a first oxygen ion conductive solid electrolyte structure comprising a first electrolyte portion having a pair of sensor cell electrodes formed on both surfaces thereof, one of said sensor cell electrodes being exposed to the measuring gas in the inner cavity and the other of said sensor cell electrodes being exposed to the reference gas, and a second electrolyte portion having a pair of detector cell electrodes formed on both surfaces thereof, one of said detector cell electrodes being exposed to the measuring gas in the inner cavity and the other of said detector cell electrodes being exposed to the reference gas in the said at least one reference gas passage, the first electrolyte portion and the pair of sensor cell electrodes constituting an oxygen sensor cell, the second electrolyte portion and the pair of detector cell electrodes constituting a detector cell, said one of the oxygen sensor cell electrodes exposed to the measuring gas in the inner cavity being made of a material which is reactive with said constituent gas, said one of the detector cell electrodes exposed to the measuring gas in the inner cavity being made of a material which is inactive with said constituent gas;

a first insulating spacer layer which includes the inner cavity formed therein laminated on the first electrolyte portion;

a second oxygen ion conductive solid electrolyte structure comprising a solid electrolyte layer having a pair of pumping cell electrodes formed on both surfaces thereof, one of said pumping cell electrodes being exposed to the measuring gas in the inner cavity and the other of said pumping cell electrodes being exposed to the measuring gas, said solid electrolyte layer and the pair of the pumping cell electrodes constituting a pumping cell, said solid electrolyte layer being laminated on the first electrolyte portion with the first insulating spacer layer interposed therebetween;

an oxygen pumping cell controller for controlling oxygen concentration in the inner cavity according to an output voltage of the oxygen sensor cell in a feed back fashion;

a detector cell driver for supplying the same level of voltage as the voltage sensed by the oxygen sensor cell to the detector cell, so that the detector cell pumps out oxygen which exists on and around a surface of said one of the detector cell electrodes exposed to the measuring gas, from the inner cavity to the said at least one reference gas passage; and an ion current detector for measuring ion current flowing through the first electrolyte, which represents the concentration of said constituent gas in the measuring gas, by detecting a current in the detector cell caused by the voltage supplied from the detector cell driver to the detector cell.

14. A solid electrolyte gas concentration detector according to claim 13, wherein said first oxygen ion conductive solid electrolyte structure comprises a single electrolyte layer and said first and second electrolyte portions are first and second portions of said single electrolyte layer.

15. A solid electrolyte gas concentration detector according to claim 13, wherein the first and second electrolyte portions are separated by an insulating material.

16. A solid electrolyte gas concentration detector according to claim 15, wherein the first and second electrolyte portions each comprise an electrolyte layer, and said insulating material is a second insulating spacer layer that is interposed therebetween.

* * * * *